United States Patent [19]

Kawahara et al.

[11] Patent Number: 4,964,801
[45] Date of Patent: Oct. 23, 1990

[54] ENDOSSEOUS IMPLANT HAVING POLYCAPILLARY STRUCTURE

[75] Inventors: Haruyuki Kawahara, Moriguchi; Katsumi Tanaka, Ninomiya; Yasuyuki Ashiura, Odawara; Motonobu Yoshimura, Samukawa, all of Japan

[73] Assignees: Haruyuki Kawahara, Osaka; Toho Titanium Co., Ltd., Tokyo, both of Japan

[21] Appl. No.: 425,513

[22] Filed: Oct. 20, 1989

Related U.S. Application Data

[63] Continuation of Ser. No. 931,661, Nov. 17, 1986, abandoned.

[30] Foreign Application Priority Data

Nov. 27, 1985 [JP] Japan .................. 60-264994

[51] Int. Cl.$^5$ .............................................. A61C 8/00
[52] U.S. Cl. ................................... 433/173; 433/176; 433/201.1
[58] Field of Search ............... 433/173, 174, 175, 176, 433/201.1

[56] References Cited

U.S. PATENT DOCUMENTS

| 3,808,606 | 5/1974 | Tronzo | 433/173 |
| 3,928,914 | 12/1975 | Kozlovsky | 433/176 |
| 4,379,694 | 4/1983 | Riess | 433/173 |
| 4,447,209 | 5/1984 | Sutter | 433/173 |
| 4,531,917 | 7/1985 | Linkow et al. | 433/176 |
| 4,536,158 | 8/1985 | Bruins et al. | 433/201.1 |

FOREIGN PATENT DOCUMENTS

| 2302715 | 11/1976 | France | 433/173 |
| 1052865 | 3/1986 | Japan | 433/176 |
| 1544412 | 4/1979 | United Kingdom | 433/173 |

*Primary Examiner*—Gene Mancene
*Assistant Examiner*—Adriene B. Lepiane
*Attorney, Agent, or Firm*—Koda & Androlia

[57] ABSTRACT

An endosseous implant including at least an embedding portion to be embedded in a living tissue, the embedding portion comprising any of a platelike body itself and a desired shape of body obtained by working the platelike body, the platelike body having orderly or disorderly a plurality of substantially straight tubular channels passing through the thickness of the platelike body for permitting the ingrowth and penetration of the adjacent bone tissue therein, the tubular channels including at least two kinds of three different pore diameters of large, medium, and small pore diameters respectively for permitting the ingrowth and penetration of a bone tissue, osteoid tissue, and fibrous tissue, whereby a polycapillary structure is built by the ingrowth and penetration of the at least two of the three kinds of tissues which pass through the thickness of the platelike body after the implantation. According to the endosseous implant, there is provided a polycapillary structure which makes it possible for at least two of the bone, osteoid and fibrous tissue to pass through the thickness of the implant to make a biological dynamic connection of hard and soft tissues by the minial two kinds of the tissue. Futhermore the distribution of the tubular channels is set depending upon the stress imparted to said embedding portion, said distribution being such that channels small in pore diameter correspond to high impact stress, channels medium in pore diameter correspond to medium impact stress, and channels large in pore diameter correspond to low impact stress.

12 Claims, 4 Drawing Sheets

ENDOSSEOUS IMPLANT HAVING POLYCAPILLARY STRUCTURE

This is a continuation of application Ser. No. 931,661, filed Nov. 17, 1986 now abandoned.

BACKGROUND OF THE INVENTION

1. Field of the Invention

This invention relates to an endosseous implant embedded in the bone tissue of a living being for use in restoring the organic functions of the being, and more particularly to an implant having a polycapillary structure by being set in the alveolar bone for use in dental prosthesis and orthopedic surgery.

2. Prior Art

Along with the development of bioengineering and development of biomaterials, a therapeutic operation is practiced for embedding in the bone tissue an implant in the form of an artificial tooth root and artificial bone in the dental treatment and orthopedic surgery fields. It is said of the prosthetic materials used in a living being that metal materials or ceramic materials least related to the bio-system are higer in stability rather than high-molecular materials having a molecular structure similar to materials constituting the living being. Furthermore, it is required of prosthetic materials for use in the living being that the materials have no irritating or toxic effect on the cells and tissues, that they make no physical and chemical changes in the living body, especially no change in mechanical strength, that they can sufficiently stand external force, and that they are excellent in adhesibility with respect to their adjacent tissues.

Included under the biomaterials that can approximately satisfy the items of requirement mentioned above are metals such as pure aurum, platinum, titanium zirconium, tantalum, auric alloy, platinic alloy, titanic alloy, zirconic alloy, cobalt-chromic alloy, ferro-nickel-chromic alloy; and ceramic materials such as aluminum oxide, zirconium dioxide, silicon nitride, apatite crystallized glass. Various proposals have been made for making an implant of a composite material of the mentioned metals and/or ceramics to make reliable fixation of the implant in bone tissue. For example, in a dental endosseous implant used as an artificial tooth root, maintenance and anchoring of the implant in the alveolar bone depends greatly upon how the bone tissue, osteoid tissue and fibrous tissue are connected with the implant surface. As a result, a blade type implant has been formed with metallic or ceramic plate with vent holes each having a uniform size called a vent and designed to maintain the implant in the alveolar bone by the anchoring effect of a bone tissue proliferating and penetrating into the vents. Also, in a porous implant in which a porous ceramic material, cement material, or a sintered body of pure titanium and a titanic alloy is used as a material, retentive force of the implant in alveolar bone tissue is achieved by an anchor-hold created between the implant and the bone tissue in growth into the pores. For example, U.S. Pat. No. 4,259,072 to the previous invention of an endosseous ceramic implant by Dr. Haruyuki Kawahara, one of the present inventors is the case in point. According to the previous invention, the implant is a composite structure made, in combination, of an outer ceramic member and an inner ceramic core member, the outer member being made of porous ceramics and being formed both on the upside and on the underside with apertures of 20-50 $\mu$m (for dental use) and being formed inside of the thickness thereof with net-like roots communicating with the apertures. A bone tissue and a connective tissue invade and pass through the apertures into the roots inside the member, with result that the outer member is stably maintained and anchored by an anchoring effect in the bone.

But the implants formed of conventionally known metals or alloys or ceramics, for example, a blade vent type and a corevent type implant have a hole of $\phi$ 1 mm or more and accordingly the implant is maintained only by the anchoring effect of the ingrowth bone tissue. But when this bone tissue is broken or damaged by a pathological cause or masticatory impact or concentration of masticatory stress, there are not a few cases bringing artificial tooth root into failure.

Also, because conventional porous implants are fragile in mechanical strength and the embedding portions of the implants are all columnar, the implants are restricted in the selection of the cases of which the use of the implant is effective and are small in the number of applications of the implants in compliance with the cases of disease.

Furthermore, since the outer member of the prior art U.S. Pat. No. 4,259,072, as previously mentioned, is obtained from porous ceramics, apertures and net-like roots are all formed of the porous structure alone, namely, the shape, size and distribution of the apertures and net-like roots are dependent upon the kind, amount of foaming agent used in forming pores and upon the sintering conditions of ceramics. Accordingly, the problem is that it is difficult in point of design to artificially control the desired shape, size and distribution of tubular channels.

In an attempt to solve the problems of the prior art, the present inventors make the following proposal by the invention they have made out after intensive research.

SUMMARY OF THE INVENTION

Namely, an object of the invention is to provide an implant capable of causing a polycapillary structure to be built or constructed therein by permitting ingrowth and penetration of at least more than two kinds of bone tissue, osteoid tissue and fibrous tissue thereinto so that hard and soft anchoring effects inherent in the tissues can be freely obtained by artificial selection of the growing and penetrating tissue correspondingly to various cases in disease. The implant, after the aforestated tissues have thus made ingrowth and penetration thereinto, is firmly supported in a manner of beams on both sides of its thickness by the tissues which have thus made ingrowth and penetration and is formed with an architectural structure of bone just as in a natural bone tissue. The object is achieved by an endosseous implant including at least an embedding portion to be embedded in a living tissue, the embedding portion comprising any of a platelike body itself and a desired shape of body obtained by working the platelike body, the platelike body having regularly or irregularly a plurality of substantially straight tubular cylindrical channels passing through the thickness of the platelike body for permitting the ingrowth and penetration of the adjacent bone tissue therein, the channels including at least two kinds of three different pore diameters of large, medium and small pore diameters respectively for permitting the ingrowth and penetration of a bone tissue, osteoid tissue, and fibrous tissue, whereby a polycapillary structure is built by the ingrowth and penetration of the at least two of the three kinds of tissues which pass through the thickness of the platelike body after the implantation. In preferred embodiments of the invention, the platelike body constituting the embedding portion comprises not only a literally straight plate but also a cylindrical body rolled into a hollow body. It should be understood from the invention that the embedding portion may also be provided in various shapes other than the platelike body.

A description will now be given of some preferred embodiments of the invention with reference to the accompanying drawings.

DETAILED DESCRIPTION OF THE INVENTION

It is desirable that the implant material used in the invention be made of a metal of simple substance such as titanium, zirconium, tantalum as a material least harmful to a living tissue; but is possible to make suitable section from metals such as titanic alloy, zirconic alloy, ferro-nickel-chromic alloy, cobalt-chromic alloy, or from ceramic materials such as alumina ceramics, zirconia ceramics, apatite crystallized glass ceramics, hydroxiapatite and ceramics, etc.

Figure 1:
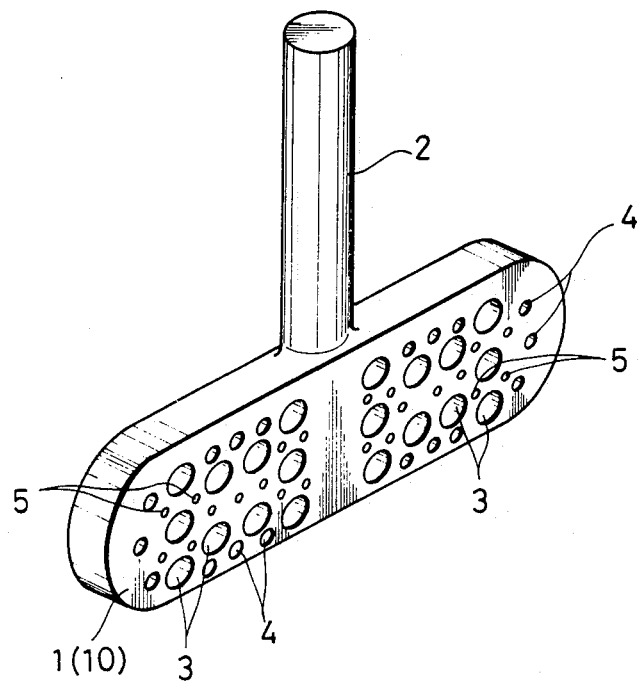
FIG. 1 is a perspective view of the endosseous implant of the invention having an embedding portion formed of a vertical plate.
Figure 2:
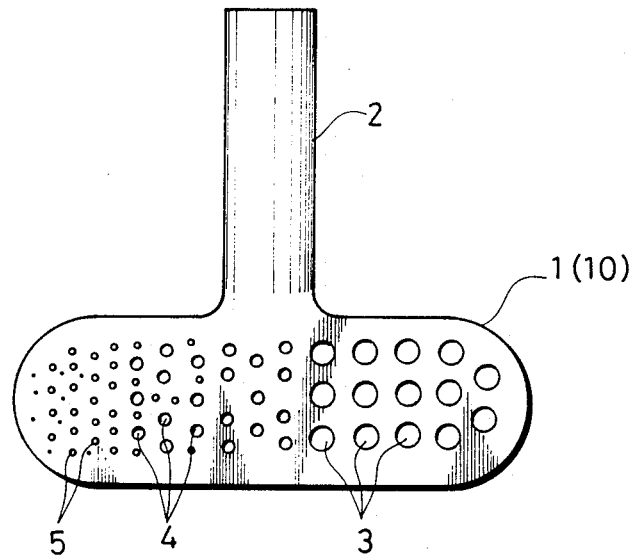
FIG. 2 is a front view showing another distribution of cylindrical channels in the implant of the same type as that of FIG. 1.
Figure 3:
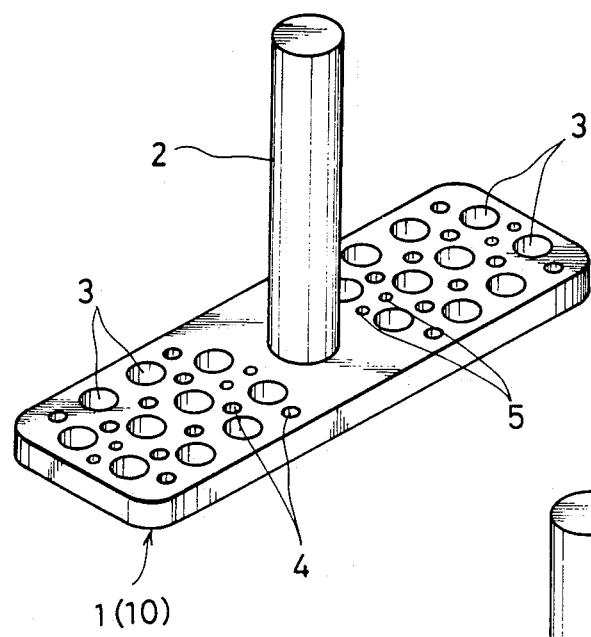
FIG. 3 is a perspective view of the implant having an embedding portion formed of a horizontal plate in another embodiment of the invention.
Figure 4:
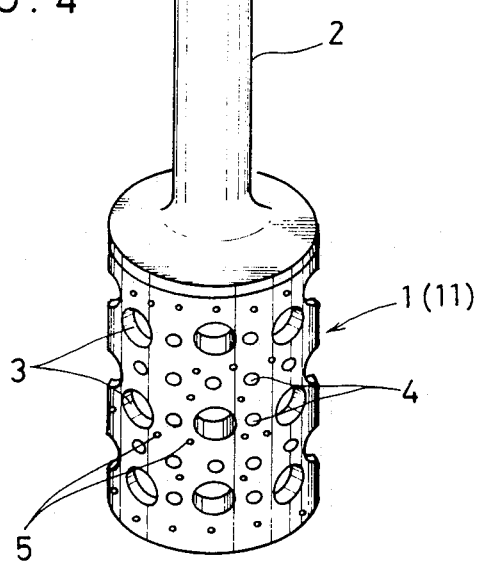
FIG. 4 is a perspective view of an embodiment wherein a plate-like body is rolled into a cylindrical body for use as an embedding portion.
Figure 5:
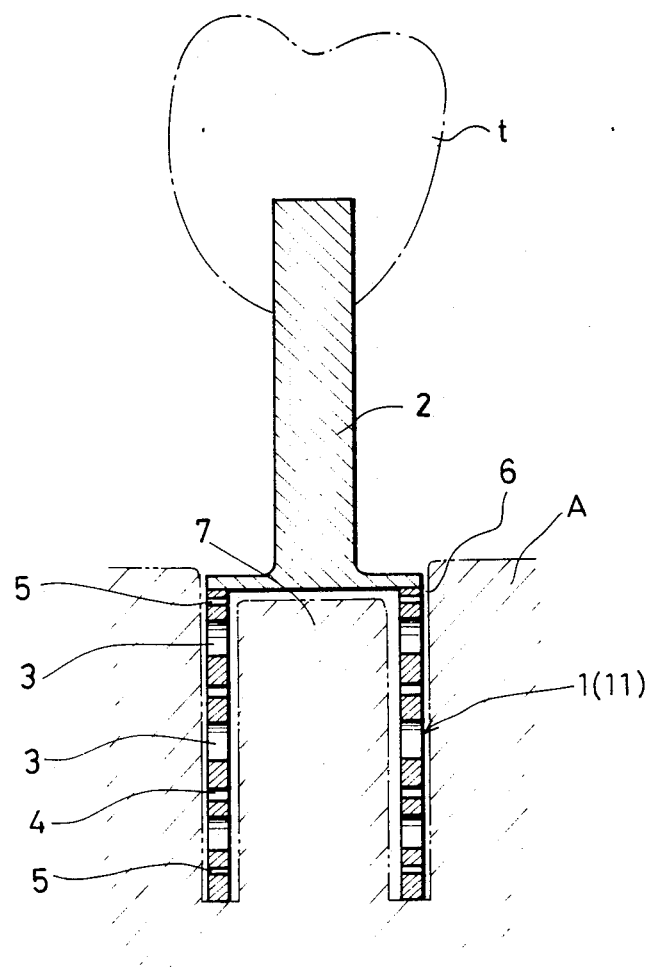
FIG. 5 is a sectional view of the FIG. 4 embodiment used in the alveolar bone.
Figure 6:
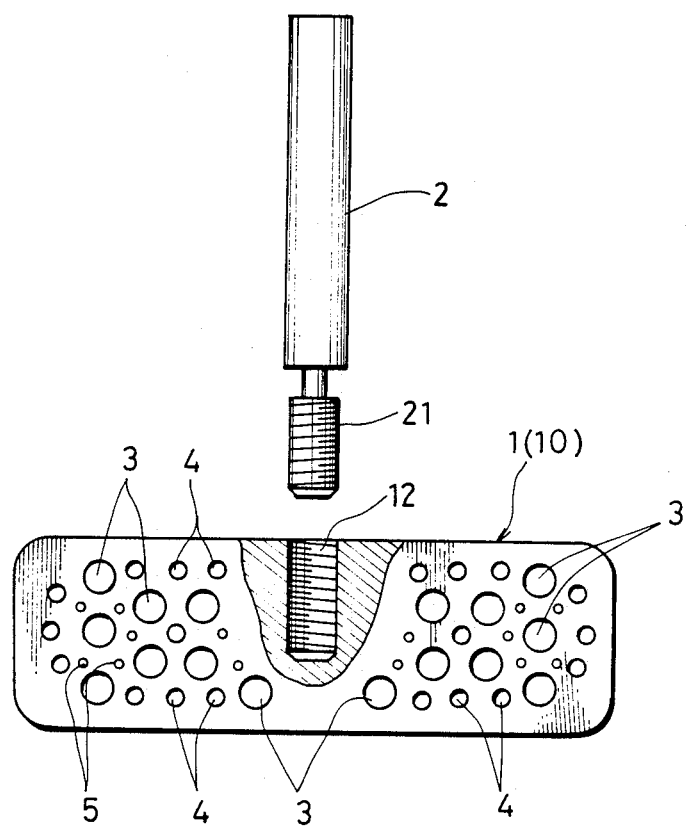
FIG. 6 is a front view, partly broken and exploded, of a submersible type implant showing still another embodiment of the invention.

A description will now be given of the details of an endosseous implant having a polycapillary structure with reference to a dental endosseous implant utilized as an artificial tooth root and shown by way of example. Shown in FIGS. 1 through 6 are all dental endosseous implants in each of which the implant includes an embedding portion 1 and a post 2 connected to the portion 1 in about the center thereof and extending upwardly of the portion 1 to receive an artificial tooth t on the top thereof (FIG. 5). With respect to the shape of a platelike body constituting the embedding portion 1, the embodiments in FIGS. 1 and 2 are made respectively of vertical plates 10, that in FIG. 3 is made of a horizontal late 10, that in FIGS. 4 and 5 is rolled into a hollow cylinder 11 by rolling a porous platelike body into the cylinder 11, and the embedding portion 1 in FIG. 6 is formed of a vertical plate in the manner that the post 2 is detachably screwed to the embedding portion by being screwed into the embedding portion. In the embodiments illustrated, the cylindrical channels 3–5 are divided into three different kinds of pore diameters which are larger pore diameter of more than 100 $\mu$m for a bone tissue (ingrowth and penetration), a medium pore diameter of 40–100 $\mu$m for an osteoid tissue ingrowth and penetration and a small pore diameter of less than 40 $\mu$m for a fibrous tissue ingrowth and penetration. The range in which these ranges of pore diameters overlap each other does not indicate restrictive range of numerical value for ingrowth and penetration of any of the above tissue, but because the tissues are living tissues, plural tissues may mixedly make ingrowth and penetration into the implant.

Formation of cylindrical channels in the invention permits suitable selection from an electrobeam process, laser beam process, electrospark machining method, and mechanical drilling method.

The implant of the polycapillary structure in the invention is different in geographical distribution of cylindrical channels from conventional porous implants and makes it possible to artificially freely set the range of pore diameter and distribution of cylindrical channels by any of the electrobeam process, laser beam process, electrospark machining method and mechanical drilling method. For example, in the embodiments illustrated, cylindrical channels 3, 4 and 5 having respectively a large pore diameter of 1000 $\mu$m (1 mm), a medium pore diameter of 100 $\mu$m (0.1 mm) and a small pore diameter of 40 $\mu$m (0.04 mm) are located closely with each other distributed disorderly, while in FIG. 2 the cylindrical channels 3, 4 and 5 are sectionally distributed in respective groups and are approximately regularly distributed in each group. The opening rate of the cylindrical channels 3, 4 and 5 in FIG. 1 is about 30% of the surface area of the vertical plate. The opening rate ranges generally from 20–60%. Such geographical distribution of cylindrical channels 3, 4 and 5 is suitably determined correspondingly to the external force imparted to the implant. Namely, ingrowth and penetration of the bone tissue into the channels 3 provides relatively rigid supporting of the implant, while because the fibrous tissue and osteoid tissue are low in modulus of elasticity and high in shock resistance and these tissues support the implant softly and is essentially not crushed or broken by any external impact. To cite an instance, even if the bone tissue which made ingrowth and penetration into the implant is broken by strong stress (particularly impact stress) and becomes unable to support the implant, supporting of the implant by fibrous tissue and/or osteoid tissue remains effective and prevents the implant from dropping off, thus allowing meantime the bone tissue to be rehealed or reformed, thereby re-insuring the firm maintenance of the implant in the alveolar bone. Accordingly, consideration is given to the distribution of tubular channels in such a manner that when the stress given to implant is strong impact, it is softly received mainly by the fibrous tissue, that when the stress is weak impact, it is rigidly received by the bone tissue, and that when the stress is medial, it is received in a harmoniously mixed state of rigidness and softness by the osteoid tissue. One of the characteristic features of the invention lies in an attempt to construct a polycapillary structure between the implant and the living tissue by ingrowth and penetration of at least two of the three tissues into the tubular channels of the implant. Because the polycapillary structure passes through the thickness of the platelike body of the embedding portion and is formed relative to straight tubular cylindrical channels unlike conventional porous implants, it is not difficult to imagine that the platelike body can be supported in the living body substantially uniformly by the ingrowth and penetration tissues in both sides of the platelike body. In this manner, the interface between the implant and its ambient bone tissue forms a biological dynamic interface to reproduce a support much like an architectural structure of bone which could be realized in a natural bone tissue. In this respect, the invention can be applied also to the case of disease which cannot be treated by a vent type implant having such a simple interface exclusively of pore more than 1 mm in diameter as is the case with the prior art. In addition thereto, when compared with the implant whose apertures in the outer member of the porous implant are not formed along the axis of channel but are formed in variously complicated relation as is the case with a netlike structure formed within the thickness of a porous implant (outer member) consisting of porous ceramics like that of the prior art, consideration in point of design given to the supporting of the implant is not only rendered easier by the manufacturing method of the invention but also a length of each tubular channel within the thickness of the implant is also reduced, so that the invention is superior to the prior art not only in the number of days during which the bone tissue, osteoid tissue and fibrous tissue make ingrowth and penetration into the implant but also in the assurance of beam-like support on both sides of the implant after the penetration. The invention can be distinguished in this respect from the prior art.

A description will now be given concretely of the invention embodied in the dental endosseous implant. Embodiments in FIGS. 1 and 2 show the case wherein when a platelike body is a vertical plate 10, a longitudinal slot (not shown) is formed in the alveolar bone to implant the plate 10 in the slot. An embodiment in FIG. 3 shows the case wherein when the platelike body is a horizontal plate 10, a recess (not shown) adapted to receive the plate 10 therein is formed in the alveolar bone to implant the plate 10 in the recess. When the platelike body is rolled into a cylindrical body 11 as shown in FIG. 4, a ringlike hole 6 slightly larger than the wall thickness of the body 11 is formed in an alveolar bone A as shown in FIG. 5, and the body 11 is set in the hole 6, so that a columnar natural bone 7 inside of the cylindrical body 11 is used as a core of the implant to render it possible for at least two tissues of a bone tissue, osteoid tissue and fibrous tissue to make ingrowth and penetration from inside and outside of the body 11 into the tubular channels 3, 4 and 5. Thus, when the time has come when the mentioned at least two kinds of tissues have made ingrowth and penetration into any two kinds of tubular channels out of the three cylindrical channels 3, 4 and 5 of the body 11, an artificial tooth t is fitted over a post 2. In this structure, since the core 7 is positioned inside the cylindrical body 11, reinforcement is provided by the core 7, so that post-operational stability of the cylindrical body 11 can be achieved at a comparatively early stage of ingrowth and penetration of the aforestated tissues into the channels 3, 4 and 5. In contrast thereto, since the outer member implanted in the alveolar bone is hollow with no core placed inside in the case of the prior art, not only is it necessary to fill the hollow outer member with some suitable material or other, but also it takes a comparatively long period of time for the penetrated tissues to sufficiently develop, differentiate and ossify. A submersible implant in FIG. 6 is of the type in which the post 2 is connected to the vertical plate with a male screw 21 and a female screw 12 in such a manner that the vertical plate 10 alone is implanted in the alveolar bone and that only after the implant having been stabilized the post 2 is threadedly connected to the vertical plate 10. In this example also, stabilization of the implanted vertical plate 10 can be achieved in a relatively short period of time by the ingrowth and penetration of the tissue into the cylindrical channels 3, 4 and 5.

In the dental endosseous implants illustrated as above, since the implant of the invention enables dynamic connection by both hard and soft tissues of the bone and fibrous tissues after the implant has been embedded in the alveolar bone, the anchoring force of the implant in the bone is strong and at the same time provides an architectural structure of bone tissue in the living bone. Accordingly, even if the bone tissue is broken by the external impact force applied to the implant and especially as by masticatory impact in time of mastication and is deprived of its anchoring effect, the implant does not detach from the alveolar bone. Namely, due to the fibrous tissue and anchoring the fibrous tissue and osteoid tissue which made ingrowth into the tubular channels each having a small pore diameter of less than 40 $\mu$m and a medium pore diameter of 40–100 $\mu$m are not broken by masticatory impact but can hold the implant in the alveolar bone, and moreover promote rehealing of the broken surface of the bony substance at the bone implant interface. According to the invention, artificial control of the kind and distribution of pore diameters is easy in point of drilling technique. Accordingly, it is possible to manufacture on a planned basis implants having various pore diameters in accordance with the cases of disease.

It is desirable to use simple metal substances which are or more harmful to living tissue as materials for use in an implant (pure titanium is used in the embodiments), but it is not objectionable to use a titanic alloy, zirconic alloy, ferro-nickel-chromic alloy or ceramic materials such as aluminum oxide, zirconium dioxide, apatite crystallized glass ceramics, hydroxiapatite, silicon nitride ceramics, etc. Wide application is expected from the invention in that the invention can find proper application as an implant for use not only in dental treatment but also in other orthopedic surgery.

Having described our invention related to the embodiments shown in the accompanying drawings, it is our intention that the invention be not limited by any of the details of description, unless otherwise specified, but rather be construed broadly within its spirit and scope set out in the accompanying claims.

I claim:

1. A method of forming a biological dynamic interface between an endosseous implant embedded in the living body and its ambient tissue, said method comprising:

preparing an endosseous implant including at least an embedding portion to be embedded in a living tissue, said embedding portion comprising any of a platelike body itself and a desired shape of body obtained by working the platelike body, said platelike body having orderly or disorderly a plurality of substantially straight tubular channels passing through a thickness of said platelike body for permitting the ingrowth and penetration of adjacent bone tissue therein, said tubular channels including at least two kinds of three different pore diameters of large, medium and small pore diameters for permitting the ingrowth and penetration of a bone tissue, osteoid tissue, and fibrous tissue, respectively wherein the tubular channels are formed by a process selected from the group consisting of an electrobeam process, laser beam process, electrospark machining method and mechanical drilling method and the distribution of said tubular channels is set depending upon the stress imparted to said embedding portion, said distribution being such that channels small in pore diameter correspond to high impact stress, channels medium in pore diameter correspond to medium impact stress, channels large in pore diameter correspond to low impact stress; and implanting said embedding portion in an endosseous area to allow the ingrowth and penetration of said at least two of the three kinds of tissues which pass through the thickness of said platelike body after the implantation to thereby build a polycapillary structure for said biological dynamic interface.

2. A method according to claim 1, wherein said platelike body is formed in a shape of a straight vertical plate or horizontal plate.

3. A method according to claim 1, wherein said platelike body is rolled into a cylindrical body.

4. A method according to claim 1, wherein the pore diameters of said tubular channels are in the range of 10–3,000 $\mu$m, said diameters being less than 40 $\mu$m in small diameter, 40–100 $\mu$m in medium diameter, and larger than 100 $\mu$m in large diameter, respectively.

5. A method according to claim 4, wherein said large pore diameter is 1000 $\mu$m, medium diameter is 100 $\mu$m and small diameter is more than 40 $\mu$m.

6. A method according to any one of claims 1 to 5, wherein all of said tubular channels, cover to 20–60% of the surface area of said platelike body.

7. A method according to claim 6, wherein said tubular channels are distributed depending upon the stress imparted to said embedding portions, said distribution being such that channels small or medium in pore diameter correspond to high impact stress, channels medium in pore diameter correspond to medium impact stress, and channels large or medium in pore diameter correspond to small impact stress.

8. A method according to claim 1, wherein a post for securing a prosthetic member thereto is connected to the embedding portion.

9. A method according to claim 8, wherein the embedding portion is implanted in an alveolar bone and an artificial tooth is fitted over a top of the post implanted in the alveolar bone.

10. A method according to claim 9, wherein said tubular channels include three different pore diameters and said embedding portion is chosen from any one of a vertical plate, a horizontal plate, and a cylindrical body formed by rolling the platelike body into a cylindrical shape.

11. A method according to claim 10, wherein a submersible type implant connected threadedly to the post is used as said vertical plate.

12. A method according to claim 10, wherein said embedding portion and said post are formed of pure titanium or a titanic alloy, said channel diameter is in the range of 10–3000 $\mu$m, and said channels in the embedding portion cover 30% of the surface area of the embedding portion.

* * * * *